US012636191B2

(12) United States Patent
Ochoa et al.

(10) Patent No.: US 12,636,191 B2
(45) Date of Patent: May 26, 2026

(54) DEVICES AND METHODS FOR IMPROVED FOLLOWABILITY IN LASER-BASED OCULAR PROCEDURES

(71) Applicant: Alcon Inc., Fribourg (CH)

(72) Inventors: Francisco Javier Ochoa, La Mirada, CA (US); John Morgan Bourne, Irvine, CA (US)

(73) Assignee: Alcon Inc., Fribourg (CH)

( * ) Notice: Subject to any disclaimer, the term of this patent is extended or adjusted under 35 U.S.C. 154(b) by 279 days.

(21) Appl. No.: 18/451,211

(22) Filed: Aug. 17, 2023

(65) Prior Publication Data

US 2024/0074902 A1      Mar. 7, 2024

Related U.S. Application Data

(60) Provisional application No. 63/374,397, filed on Sep. 2, 2022.

(51) Int. Cl.
*A61F 9/008*        (2006.01)
*A61B 90/30*        (2016.01)

(52) U.S. Cl.
CPC .......... *A61F 9/00825* (2013.01); *A61B 90/30* (2016.02); *A61B 2090/306* (2016.02); *A61F 2009/00887* (2013.01)

(58) Field of Classification Search
CPC .................................................. A61F 9/00825
See application file for complete search history.

(56) References Cited

U.S. PATENT DOCUMENTS

| | | | |
|---|---|---|---|
| 4,694,828 A | 9/1987 | Eichenbaum | |
| 5,318,560 A | 6/1994 | Blount et al. | |
| 5,372,595 A | * 12/1994 | Gaasterland | ............ A61F 9/008 606/4 |
| 6,096,028 A | 8/2000 | Bahmanyar | |
| 6,454,763 B1 | 9/2002 | Motter | |
| 8,900,139 B2 | 12/2014 | Yadlowsky | |
| 8,951,244 B2 | 2/2015 | Smith | |
| 8,968,347 B2 | 3/2015 | McCollam | |

(Continued)

FOREIGN PATENT DOCUMENTS

| | | |
|---|---|---|
| EP | 0335714 A2 | 10/1989 |
| WO | 9524867 A1 | 9/1995 |
| WO | 2011102870 A1 | 8/2011 |

OTHER PUBLICATIONS

Dular, Matevz et al., "High speed observation of damage created by a collapse of a single cavitation bubble", Wear 418-419 (available online Nov. 8, 2018), pp. 13-23.

*Primary Examiner* — Eric D. Bertram

(74) *Attorney, Agent, or Firm* — Patterson + Sheridan, LLP

(57)        ABSTRACT

Devices and methods are disclosed for improved followability in laser-based ocular procedures. In some embodiments, an ophthalmic instrument comprises a projection located at the distal end of the shaft or cannula, the projection having a distal surface in proximity to the distal end of the optical fiber, the distal surface adapted to be positioned facing the treatment area during use of the ophthalmic instrument. An example method includes delivering laser energy through an optical fiber to the treatment area, wherein the distal surface of the projection inhibits bubbles formed during the procedure from moving distally away from the distal end of the ophthalmic instrument.

20 Claims, 3 Drawing Sheets

(56) References Cited

U.S. PATENT DOCUMENTS

| | | | |
|---|---|---|---|
| 9,028,400 B2 | 5/2015 | Yadlowsky et al. | |
| 9,681,793 B2 | 6/2017 | Artsyukhovich | |
| 9,931,447 B2 | 4/2018 | Layser | |
| 10,016,248 B2 | 7/2018 | Mirsepassi | |
| 10,238,543 B2 | 3/2019 | Farley | |
| 10,244,931 B2 | 4/2019 | Kern | |
| 10,307,290 B2 | 6/2019 | Kern | |
| 10,376,414 B2 | 8/2019 | Hallen | |
| 10,537,472 B2 | 1/2020 | Brennan | |
| 10,639,198 B2 | 5/2020 | Farley | |
| 10,869,735 B2 | 12/2020 | Diao et al. | |
| 11,109,938 B2 | 9/2021 | Horn et al. | |
| 11,173,008 B2 | 11/2021 | Mirsepassi et al. | |
| 11,213,426 B2 | 1/2022 | Cook et al. | |
| 11,369,452 B2 | 6/2022 | Bacher et al. | |
| 11,471,242 B1 | 10/2022 | Diao | |
| 11,628,091 B2 | 4/2023 | Diao et al. | |
| 11,684,515 B2 | 6/2023 | Diao et al. | |
| 2010/0076419 A1* | 3/2010 | Chew ..................... | A61F 9/009 |
| | | | 606/6 |
| 2011/0144641 A1 | 6/2011 | Dimalanta, Jr. | |
| 2012/0330102 A1* | 12/2012 | Brennan ........... | A61B 1/00165 |
| | | | 600/177 |
| 2015/0374539 A1* | 12/2015 | Buzawa ............. | A61F 9/00781 |
| | | | 606/4 |
| 2017/0014023 A1* | 1/2017 | Kern ........................ | A61B 1/07 |
| 2018/0360657 A1 | 12/2018 | Bor et al. | |
| 2019/0201238 A1* | 7/2019 | Bacher .................... | A61F 9/008 |
| 2021/0137739 A1 | 5/2021 | Kraemer | |
| 2021/0186755 A1* | 6/2021 | Khoo ..................... | A61F 9/009 |
| 2021/0290438 A1 | 9/2021 | Hallen | |
| 2023/0116921 A1 | 4/2023 | Jung et al. | |
| 2023/0181367 A1 | 6/2023 | Farley et al. | |
| 2025/0275871 A1* | 9/2025 | Ochoa .................... | A61M 1/77 |

* cited by examiner

DEVICES AND METHODS FOR IMPROVED FOLLOWABILITY IN LASER-BASED OCULAR PROCEDURES

TECHNICAL FIELD

The present disclosure is directed to devices and methods for improved followability in laser-based ocular procedures.

BACKGROUND

Lasers are used in many different medical procedures including a number of different ophthalmic procedures. For example, lasers may be used in cataract surgery, such as for fragmenting and/or emulsifying the cataractous lens. In some procedures, a laser is used for initial fragmentation of the lens, followed by phacoemulsification of the lens by an ultrasonic handpiece to complete the breakdown of the lens for removal. In other procedures, the laser may be used for complete fragmentation and/or emulsification of the lens for removal, without the need for a separate application of ultrasonic energy. Lasers may also be used for other steps in cataract surgery, such as for making the corneal incision(s) and/or opening the capsule.

U.S. Patent Application Publication No. 2018/0360657 discloses examples of an ophthalmic laser system. That application describes laser uses such as for forming surgical cuts or for photodisrupting ophthalmic tissue as well as for cataract surgery, such as laser-assisted cataract surgery (LACS). U.S. Patent Application Publication No. 2019/0201238 discloses other examples of an ophthalmic laser system. That application describes laser uses such as in a vitrectomy probe for severing or breaking vitreous fibers. U.S. Patent Application Publication No. 2018/0360657 and U.S. Patent Application Publication No. 2019/0201238 are expressly incorporated by reference herein in their entirety.

Some laser systems emit pulses, with the pulses having a desired duration and repetition rate. Operating a laser in pulses can achieve desirable power and energy characteristics for a particular application.

A fundamental mechanism for emulsifying or disrupting lens or other ocular tissues (e.g., in cataract surgery) is by delivering laser energy, of appropriate wavelength and pulse duration, to the tip of an optical fiber (e.g., a sapphire optical fiber). The laser induces a plasma zone immediately in front of the optical surface(s) due to the surrounding material's absorption of the laser energy. The laser-induced plasma nucleates the birth of a bubble, which serves to disrupt its surroundings by the expanding and subsequent collapsing of the bubble. When lens, cataractous lens, and other ocular tissues are present in the bubble zone they may be broken apart and emulsified by the laser bubble action.

SUMMARY

The present disclosure is directed to devices and methods for improved followability in laser-based ocular procedures.

In some embodiments, an ophthalmic instrument comprises a shaft having a distal end adapted to be inserted into the eye of a patient toward a treatment area, an optical fiber for delivering laser energy to the treatment area, the optical fiber having a distal end adapted to be positioned facing the treatment area during use of the ophthalmic instrument, and a projection located at the distal end of the shaft, the projection having a distal surface in proximity to the distal end of the optical fiber, the distal surface adapted to be positioned facing the treatment area during use of the ophthalmic instrument.

In some embodiments, a surface area of the distal surface of the projection is at least two times greater than a surface area of an end face of the shaft. In some embodiments, the surface area of the distal surface of the projection may be at least eight times greater than the surface area of the end face of the shaft. In some embodiments, the distal surface of the projection has a length of 0.020 inches to 0.090 inches and a width of 0.020 inches to 0.060 inches. Smaller or larger lengths and/or widths may be used.

In some embodiments, the shaft is tubular. The optical fiber may be located inside of the shaft. In other embodiments, the optical fiber may be located outside of the shaft. The shaft may be a cannula adapted for aspiration from the treatment area.

In some embodiments, the ophthalmic instrument may comprise a tip positioned on the distal end of the shaft, wherein the projection is part of the tip. The tip may be transparent. The tip may be comprised of a polymeric material, such as polycarbonate.

The ophthalmic instrument may comprise an irrigation sleeve. The irrigation sleeve may comprise a proximal hub adapted to be coupled to a housing of the ophthalmic instrument and a distal tube adapted to fit around the shaft. The distal tube of the irrigation sleeve may have a distal end, an end opening at its distal end adapted to fit around the distal end of the shaft, and at least one side opening at its distal end proximate to the end opening adapted for irrigation fluid to flow therethrough.

In some embodiments, the projection may be part of the irrigation sleeve. The irrigation sleeve may be comprised of an elastomeric material, such as silicone rubber.

The shaft may have a longitudinal axis, and the projection may be asymmetrical about the longitudinal axis of the shaft. The projection may be angled with respect to the longitudinal axis of the shaft.

In some embodiments, a method of performing an ophthalmic surgical procedure comprises inserting a distal end of an ophthalmic instrument into the eye of a patient toward a treatment area, the ophthalmic instrument comprising a shaft, an optical fiber, and a projection; positioning the distal end of the ophthalmic instrument adjacent the treatment area such that a distal end of the optical fiber faces the treatment area and such that a distal surface of the projection faces the treatment area; and delivering laser energy through the optical fiber to the treatment area; wherein the distal surface of the projection acts to inhibit bubbles formed during the procedure from moving distally away from the distal end of the ophthalmic instrument.

Further examples and features of embodiments of the invention will be evident from the drawings and detailed description.

BRIEF DESCRIPTION OF THE DRAWINGS

The accompanying drawings illustrate example implementations of the systems and methods disclosed herein and, together with the description, serve to explain the principles of the present disclosure.

Figures 1, 2:
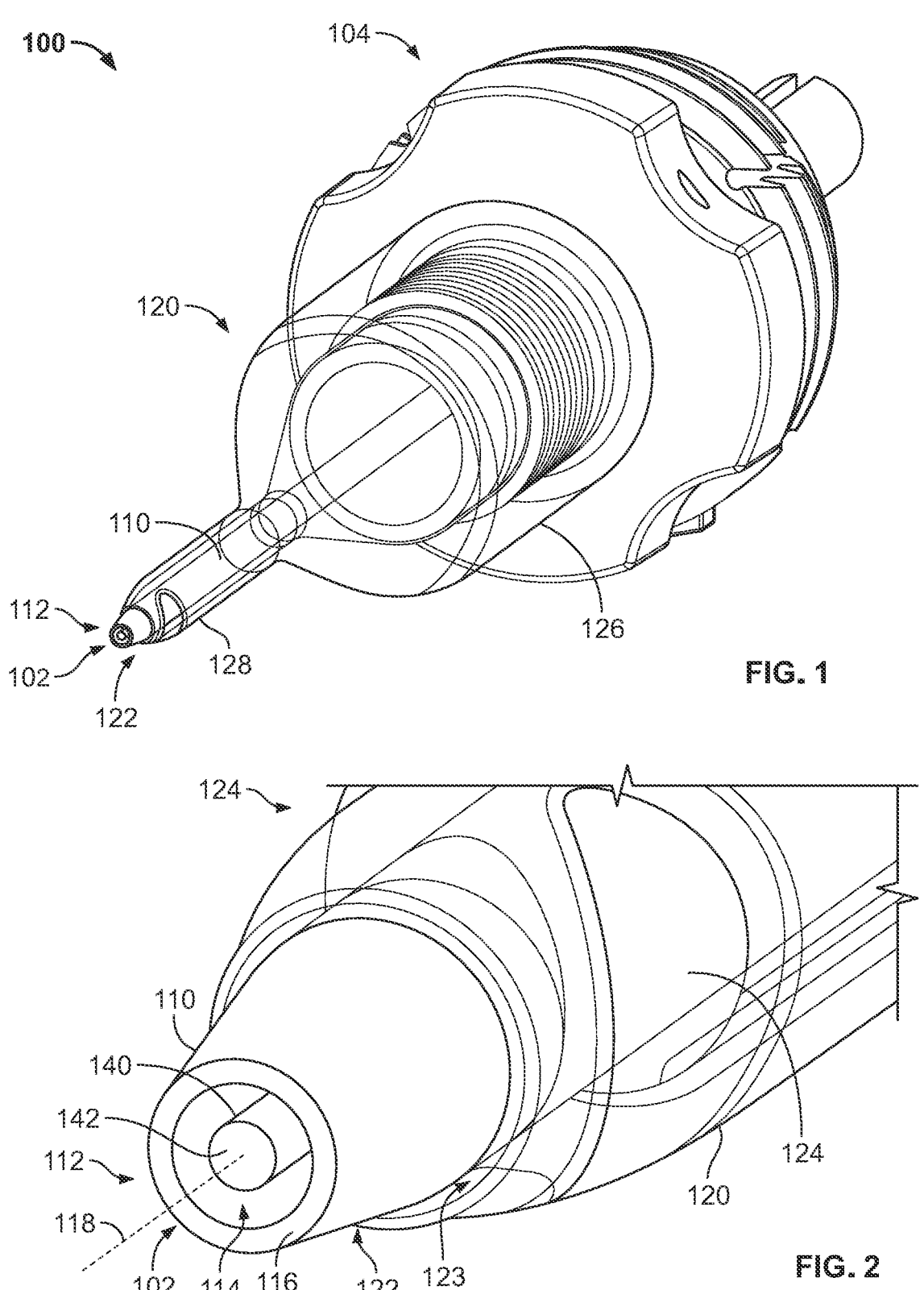
FIG. 1 shows an example of an ophthalmic instrument with a laser optical fiber.
FIG. 2 shows an enlarged view of the distal end of the ophthalmic instrument of FIG. 1.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe those implementations and other implementations. It will nevertheless be understood that no limitation of the scope of the claims is intended by the examples shown in the drawings or described herein. Any alterations and further modifications to the illustrated or described systems, devices, instruments, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure. For simplicity, in some instances the same reference numbers are used throughout the drawings to refer to the same or like parts.

The designations "first" and "second" as used herein are not meant to indicate or imply any particular positioning or other characteristic. Rather, when the designations "first" and "second" are used herein, they are used only to distinguish one component from another. The terms "attached," "connected," "coupled," and the like mean attachment, connection, coupling, etc., of one part to another either directly or indirectly through one or more other parts, unless direct or indirect attachment, connection, coupling, etc., is specified.

An ophthalmic instrument as described herein may be used with an ophthalmic surgical console. The ophthalmic surgical console may be similar to ophthalmic surgical consoles as shown and described in U.S. Pat. No. 9,931,447, the entire disclosure of which is hereby expressly incorporated herein by reference. The ophthalmic surgical console may be similar to ophthalmic surgical consoles that have been known and used, such as the CENTURION® Vision System available from Alcon Laboratories, Inc. (Fort Worth, Texas) or the CONSTELLATION® Vision System available from Alcon Laboratories, Inc. (Fort Worth, Texas), or any other ophthalmic surgical console suitable for use with the principles described herein.

The surgical console may include one or more systems that may be used in performing an ophthalmic surgical procedure. For example, the surgical console may include a fluidics system that includes an irrigation system for delivering fluid to the eye and/or an aspiration system for aspirating fluid and other material from the eye.

An example surgical system in accordance with this disclosure may include a laser system suitable for one or more ophthalmic procedures. The laser system may comprise a laser that may be housed within the surgical console or elsewhere, such as in a separate console that communicates with the surgical console. The laser system may have other components. For example, the laser system may include components for operating the laser, such as a power supply, controller, laser pumps, laser energy control, and/or monitor. In addition, the laser system may include components in the optical path of the laser output, such as one or more lenses, mirrors, and/or optical fibers.

In some embodiments, the laser system may be suitable for cataract surgery. In some embodiments, the output energy of the laser system is suitable for fragmentation and/or emulsification a cataractous lens. In some examples, the laser output is used for fragmentation and/or emulsification of the lens to a sufficient degree for removal of the lens.

The laser may be any type of laser suitable for the desired application. The laser may output suitable electromagnetic radiation at any suitable wavelength. For example, the laser may emit electromagnetic radiation in one or more wavelengths in the visible, infrared, and/or ultraviolet wavelengths. The laser may operate or be operated to emit a continuous beam of electromagnetic radiation. Alternatively, the laser may operate or be operated to emit a pulsed beam.

In one example, the laser operates in the infrared range. For example, the laser may output electromagnetic radiation in the mid-infrared range, for example in a wavelength range of about 2.0 microns to about 4.0 microns. Some examples wavelengths include about 2.5 microns to about 3.5 microns, such as about 2.775 microns, about 2.8 microns, or about 3.0 microns. Such a laser may be suitable, for example, for lens fragmentation or emulsification in cataract surgery, or for other procedures.

The laser system is designed to direct the laser electromagnetic radiation from the laser to an output port. The laser system may direct the laser electromagnetic radiation from the laser to the output port through one or more optical components, such as lenses and mirrors.

An ophthalmic instrument may be optically connected to the laser system to receive the laser electromagnetic radiation from the output port. The ophthalmic instrument may be, for example, a handpiece for an ophthalmic procedure. The instrument (e.g., handpiece) may be connected to the laser system, e.g., by a cable with an optical fiber. The connection (e.g., cable) may be flexible and relatively long to give the operator flexibility in maneuvering the handpiece at some distance away from the laser system. The laser electromagnetic radiation may be transmitted from the laser system through the optical fiber of the connecting cable to the handpiece. The optical fiber of the connecting cable may continue through the handpiece or may be optically connected to an optical fiber in the handpiece. In either case, the handpiece may include an optical fiber that terminates in a distal end at the distal end of the handpiece. The optical fiber carries the laser electromagnetic energy from the laser and emits it from the distal end of the optical fiber at the distal end of the handpiece to the desired target, such as a lens or lens fragment in the eye of a patient.

As mentioned above, the ophthalmic instrument may be connected to the control console or laser system by a cable with one or more optical fibers for delivering laser energy. The ophthalmic instrument may also have one or more other connections to the console or control system. For example, the ophthalmic instrument may be connected to the control console by one or more irrigation tubes for supplying an irrigation fluid from the control console to the instrument and/or one or more aspiration tubes for providing suction and aspiration through the instrument.

FIG. 1 shows an example of an ophthalmic instrument 100 with a laser optical fiber 140, e.g., a sapphire optical fiber. FIG. 2 shows an enlarged view of the distal end 102 of the ophthalmic instrument 100 of FIG. 1.

The ophthalmic instrument 100 comprises a housing 104 and a shaft 110, e.g., a cannula or other shaft, that extends from the distal end of the housing 104. The housing 104 may be hollow with an internal chamber in which internal components of the instrument 100 may be housed and protected. The housing 104 may have an external surface that can be grasped by an operator of the instrument 100, such as a surgeon.

The shaft 110 may be tubular, e.g., a hollow tube such as a cannula, that has an opening 114 at its distal end 112 which may be used for aspiration. For example, by applying suction through an aspiration channel from the proximal end of an aspiration luer at the proximal end of the housing 104, fluid and/or tissue, such as lens or other tissue fragments, may be aspirated through the opening 114 in the distal end 112 of the shaft 110.

The optical fiber 140 may be located inside of the shaft 110, as shown. In other embodiments, the optical fiber 140 may be located outside of the shaft 110. The optical fiber tip 142 may be flush (in the same plane as) the end face 116 of the shaft 110. In other embodiments, the optical fiber tip 142 may extend beyond the end face 116 of the shaft 110, or the end face 116 of the shaft 110 may extend beyond the optical fiber tip 142. The optical fiber tip 142 does not need to be inside of the aspiration port 114 but only in close proximity so that the material affected by the laser action can be readily aspirated.

The ophthalmic instrument 100 may also include an irrigation sleeve 120. The irrigation sleeve 120 may serve to direct an irrigation fluid, e.g., saline, to the distal end 102 of the instrument 100. The housing 104 may have an irrigation supply line through which an irrigation fluid may be introduced. The irrigation sleeve 120 may be coupled directly to the housing 104 or coupled to the housing 104 through another part of the ophthalmic instrument 100. In one example, the housing 104 may have external threads at its distal end, and the irrigation sleeve 120 may have internal threads at its proximal end, by which the irrigation sleeve 120 may be attached to the housing 104. As can be seen in FIG. 1, the irrigation sleeve 120 generally has a proximal hub 126 having a relatively larger diameter for coupling to the housing 104 and a distal tube 128 in the shape of a narrow tube having a relatively smaller diameter for fitting around the shaft 110 at a small enough dimension for inserting through an incision in an eye.

In the illustrated example, the irrigation sleeve 120 is positioned around the shaft 110 to provide a fluid passageway or channel from the position of its attachment to the housing 104 through the space between the irrigation sleeve 120 and the shaft 110. The irrigation sleeve 120 may have an end opening 123 at its distal end 122 through which the distal end 112 of the shaft 110 extends and one or more side openings 124 at its distal end 122 adjacent to the end opening 123. At the end opening 123, the irrigation sleeve 120 has a snug fit around the shaft 110. When an irrigation fluid is introduced through the supply line in the housing 104, it passes through the channel of the irrigation sleeve 120 and out of the side opening(s) 124 at the distal end 122 of the irrigation sleeve 120.

As an example, the distal tube 128 of the irrigation sleeve 120 may have an outer diameter in a range of 0.030 inches to 0.080 inches to fit through an incision in an eye and an inner diameter in a range of 0.020 inches to 0.070 inches to accommodate the shaft 110. The end opening 123 at the distal end 122 of the irrigation sleeve 120 through which the distal end 112 of the shaft 110 projects may be a circular opening having a diameter in a range of 0.010 inches to 0.065 inches, which may be equal to or slightly smaller than the outer diameter of the distal end 112 of the shaft 110 to form a snug fit around the distal end 112 of the shaft 110. The examples of dimensions and ranges of dimensions represent possible embodiments; other embodiments with different dimensions may be used.

The irrigation sleeve 120 may be made of an elastomeric material such as a compliant silicone rubber. The irrigation sleeve 120 alternatively may be made of other materials, such as polyurethane, ethylene propylene, neoprene, or other suitable materials. An elastomeric material for the irrigation sleeve 120 allows some compliance and facilitates the snug fit between irrigation sleeve 120 and the shaft 110 at the area of the end opening 123. An elastomeric material for the irrigation sleeve 120 also facilitates a seal or snug fit between the irrigation sleeve 120 and the adjacent eye tissue at the incision site, such as the cornea or sclera, which can help minimize leakage from the eye between the eye tissue and the irrigation sleeve 120.

In operation of the device, the operator inserts the distal end 102 of the ophthalmic instrument 100 through a suitable incision in a patient's eye and positions the distal end 102 of the ophthalmic instrument 100 at a desired location, such as adjacent a cataractous lens of a patient. The distal end 112 of the shaft 110 is directed toward a treatment area, with the tip 142 at the distal end of the optical fiber 140 positioned facing the treatment area. Irrigation fluid such as saline may be supplied from the control console through the irrigation supply line and irrigation sleeve 120, such that it flows out of the side opening(s) 124 to the target area. The laser may be activated to emit laser energy from the tip 142 of the optical fiber 140 (i.e., the distal end of the optical fiber 140), which can break up and emulsify the desired tissue, such as the cataractous lens. At the same time, a pumping module may be used to apply suction through the shaft 110, thereby suctioning through the opening 114 fluid and tissue and/or lens fragments that have been separated by the action of the laser.

Figures 3, 4:
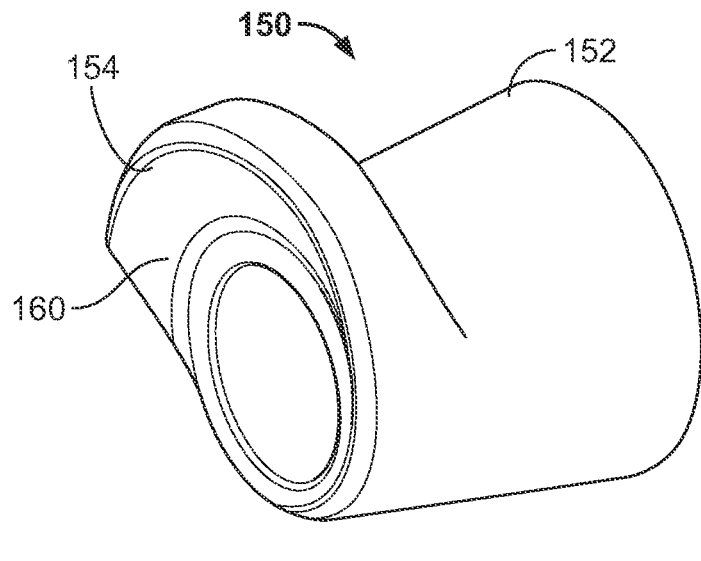
FIG. 3 shows a tip for an ophthalmic instrument in accordance with an embodiment of the disclosure.
FIG. 4 shows the distal end of an ophthalmic instrument with the tip of FIG. 3 in accordance with an embodiment of the disclosure.
Figures 5, 6:
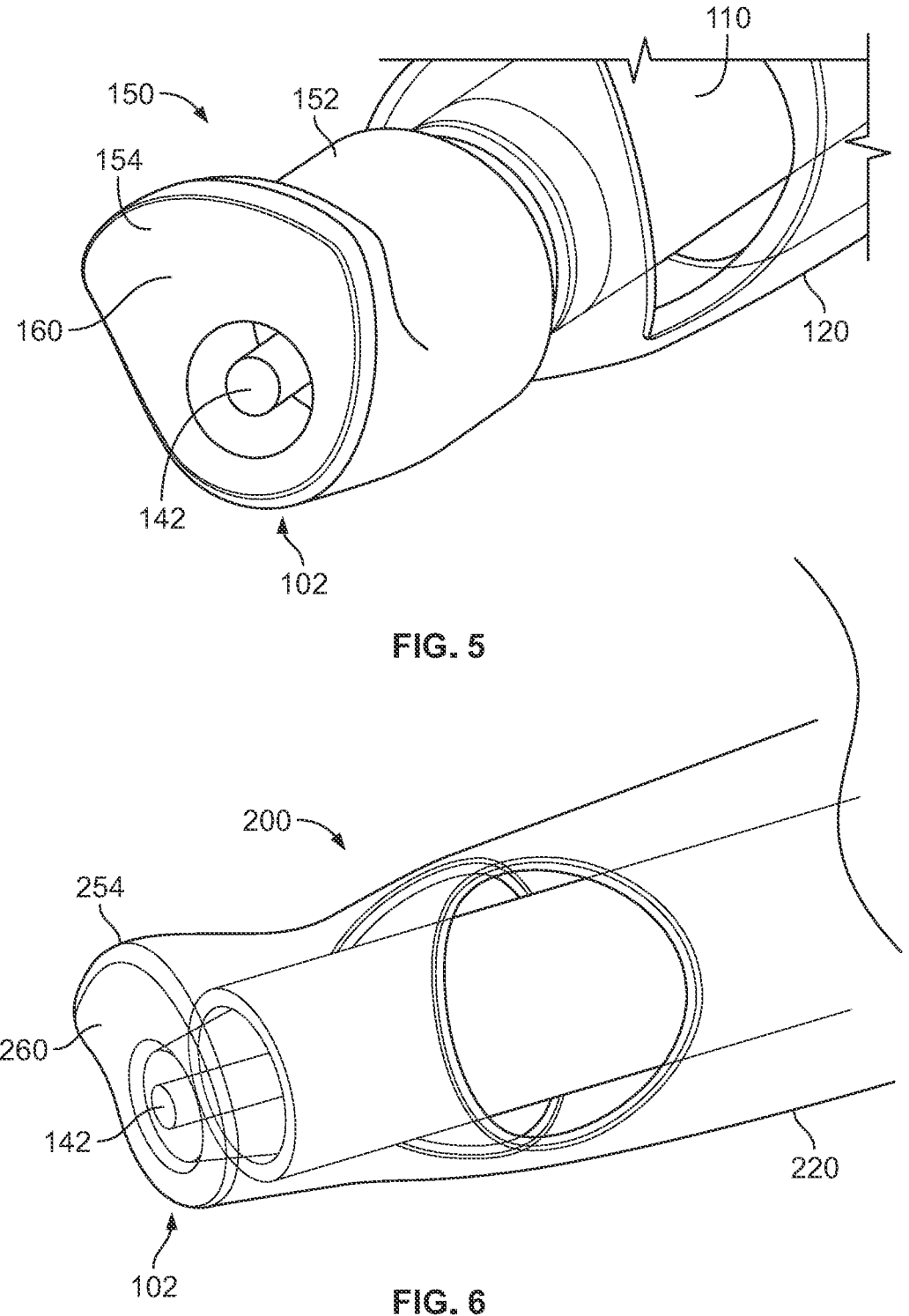
FIG. 5 shows another view of the distal end of the ophthalmic instrument of FIG. 4.
FIG. 6 shows the distal end of an ophthalmic instrument in accordance with another embodiment of the disclosure.

FIG. 3 shows a tip 150 for an ophthalmic instrument 100 in accordance with an embodiment of the disclosure. FIG. 4 shows the distal end 102 of an ophthalmic instrument 100 with the tip 150 of FIG. 3. FIG. 5 shows another view of the distal end 102 of the ophthalmic instrument 100 of FIG. 4.

The tip 150 has a cylindrical hub 152 and a projection 154. The cylindrical hub 152 is adapted to fit over and on the distal end 112 of the shaft 110, as can be seen in FIGS. 4 and 5. In this illustrated example, the tip 150 has a center hole that provides an entranceway to the channel of the shaft 110 for aspiration. In this illustrated example, the optical fiber 140 is located inside of the shaft 110 and inside of the center hole of the tip 150. In an alternative example, the tip 150 again has a center hole that provides an entranceway to the channel of the shaft 110 for aspiration, but the optical fiber 140 is located outside of the shaft 110, and the optical fiber 140 is located either inside or outside of the center hole of the tip 150. Locating the optical fiber 140 outside of the shaft 110 in some embodiments can help reduce clogging of the aspiration channel, by having the laser action offset from the aspiration channel.

With the tip 150 as part of the instrument 100 as shown in FIGS. 4 and 5, the projection 154 is located at the distal end 112 of the shaft 110 and at the distal end 102 of the instrument 100. The projection 154 has a distal surface 160 in proximity to the distal tip 142 of the optical fiber 140. The distal surface 160 faces the area to which the optical fiber tip 142 is directed. When the instrument 100 is in use with the optical fiber tip 142 facing the treatment area, the distal surface 160 also faces the treatment area.

The projection 154 with distal surface 160 provides a surface area facing the treatment area that is significantly larger than would otherwise face the treatment area. For example, in the illustrated instrument 100, without the projection 154, the end face 116 of the shaft 110 (see FIG. 2) would be the only surface facing the treatment area aside from the tip 142 of the optical fiber 140 itself. The projection 154 provides a significantly larger surface area facing the treatment area as compared to the end face 116 of the shaft 110.

In one example, the end face 116 has an outer diameter of 0.0243 inches and an inner diameter of 0.0187 inches, with a surface area of 0.000198 square inches. In one example of the projection 154, the surface area of the distal surface 160 facing the treatment area is 0.00164 square inches. Thus, in this example, the surface area of the distal surface 160 of the projection 154 is more than eight times greater than the surface area of the end face 116 of the shaft 110.

In other examples, a surface area of the distal surface 160 of the projection 154 may be at least two times greater than a surface area of the end face 116 of the shaft 110, or at least four times greater than a surface area of the end face 116 of the shaft 110, or at least six times greater than a surface area of the end face 116 of the shaft 110. The distal surface 160 of the projection 154 may have a length of 0.020 inches to 0.090 inches and a width of 0.020 inches to 0.060 inches. Smaller or larger lengths and/or widths may be used. In one example, the distal surface 160 of the projection 154 has a length of about 0.050 inches and a width of about 0.020 inches. The distal surface 160 of the projection 154 may be dished or curved in whole or in part, thereby presenting a concave surface facing the treatment area, in better conformity to the shape of the bubbles induced by the laser action.

The projection 154, with its distal surface 160 presenting a surface area that faces the area treated by the laser, helps inhibit the bubbles formed by the laser from moving away from the optical fiber tip 142. Without the surface area of the projection, the action of the laser and the bubble dynamics can, in certain situations, cause the bubbles formed by the laser to move away from the distal end of the instrument. This can reduce the efficiency of the laser action or otherwise detrimentally affect the performance of the instrument.

The problem is best understood by the behavior of a bubble, nucleated at the tip of a laser fiber without an adjacent surface such as distal surface 160 of the projection 154, as the bubble goes through its lifecycle from nucleation to collapse. As mentioned above, emulsifying or disrupting lens or other ocular tissues (e.g., in cataract surgery) may be achieved by delivering laser energy, of appropriate wavelength and pulse duration (e.g., short laser pulses), to the tip of an optical fiber. If the fiber is submerged in a medium that can readily absorb the laser energy, then a plasma zone is generated at the fiber tip. The vaporized material will begin to expand into a bubble.

In the lifecycle, the bubble begins to expand moments after the laser energy delivery. The bubble continues expanding until a maximum diameter is reached. The maximum bubble size depends upon the amount of energy delivered to the tip of the fiber. In an example, the bubble may grow to envelop the delivery fiber. The bubble may displace fluid at is expands.

In a typical bubble lifecycle, after reaching its maximum diameter, the bubble begins to collapse. As the bubble collapses, due to the presence of the optical fiber, the wall of the bubble near the optical fiber may collapse at a faster rate than the front of the bubble (opposite the fiber). Typically, when the wall of the bubble reaches the tip of the optical fiber it separates from the optical fiber but continues to collapse.

At this point, the detached bubble is typically asymmetric as the detached wall penetrates the bubble. The center of the bubble is no longer at the front face of the fiber, which was the origin of the bubble nucleation. In a continuation of the lifecycle of the bubble formed by a system without an adjacent surface such as distal surface 160 of the projection 154, the bubble attains forward momentum or repulsion away from the fiber.

In a continuation of the typical bubble lifecycle, a few moments later the bubble completely collapses once again, creating very high pressure and temperature, which will once again rebound or create another bubble expansion. With a typical bubble formation (without an adjacent surface such as distal surface 160 of the projection 154), the bubble may become significantly moved or repulsed away from the original location. The second bubble may also collapse and once again rebound before the energy is completely dissipated by the surrounding medium. The completed bubble may be substantially moved away from the location of nucleation.

A potential problem is that along with the disruptive (tissue cutting/ablating) effects of the laser energy and the bubble dynamics, there can be a repulsive effect, which can be detrimental to the efficiency of the system. The repulsion generated by the system can tend to push away the material that the operator is working on. When this method is employed to emulsify cataractous lenses, the cutting action will typically be combined with an irrigation and aspiration system. The aspiration can help reduce the issue of repulsion for laser systems in which the repetition rate of the laser is very low (e.g., 50 Hz or lower) or if there are pauses in the firing of the laser. If higher laser power or material cutting rates are desired, then aspiration rates (e.g., rates of up 40 cc/min) may not suffice to control the repulsive action of the laser. Higher material cutting rates may be in the range of 1500 Hz (repetition rate) or even higher.

Thus, without a projection and associated surface area facing the treatment area (e.g., projection 154 with distal surface 160), a system may have good holding power for high vacuum levels or low power settings, but at higher laser power settings the laser action and bubble dynamics may cause repulsion of the resultant bubbles. Accordingly, the cutting power or emulsification efficiency decreases significantly, since the target tissue or material is being moved away from the distal end of the instrument tip as opposed to broken up and aspirated into the cannula.

The use of a projection (e.g., projection 154) with a significant surface area facing the treatment area (e.g., surface area of distal surface 160) helps inhibit the distal movement of the bubble action from the optical fiber tip 142. At minimum, it reduces the repulsive effects of the laser-induced bubble dynamics. In some embodiments, it can reverse the effect such that repulsion becomes attraction. In cataract surgical terms, the use of a projection with its surface area facing the treatment area improves followability.

The followability is improved because the projection with its surface facing the treatment area causes the collapsing of a bubble to tend to collapse toward that surface. When a bubble is nucleated near a solid boundary (e.g., which is approximately equal or larger than the maximum bubble), then upon collapse the bubble will tend to collapse into the boundary.

This phenomenon can be understood by considering the mass flux as a bubble near such a solid boundary begins to collapse. As the bubble begins to collapse, fluid mass from the surrounding medium moves in to fill the void, but the "filling" is not symmetric due to the presence of the adjacent solid boundary. Since the solid boundary serves as a restrictor, mass cannot flow in from this location. Therefore, the net effect is to collapse the bubble toward the solid boundary, thus minimizing repulsion and potentially creating fluid flow toward the solid boundary.

With the use of a projection (e.g., projection 154) with a significant surface area facing the treatment area (e.g., surface area of distal surface 160), the bubble dynamics are transformed such that movement of the bubble away from the instrument is inhibited or reduced. In some embodiments, the bubble will collapse into the cannula, minimizing or even negating repulsion completely.

Thus, in summary, by equipping the distal end of the instrument with a fitting or modifying it in such a way that a surface is created to "catch" the bubble, the repulsive effects of the laser action and subsequent bubble collapse can be significantly diminished. The surface serves to capture the bubble and force it to implode inward, or serves to provide a force on the bubble toward the instrument, thereby minimizing repulsion.

The shape of the projection and its distal surface can control the way the bubble collapses. In one example, the tip 150 with the projection 154 is a plastic part that is added to the shaft 110, e.g., a metal cannula. The projection can also be shaped out of the shaft or cannula itself. The shape of the projection can have different configurations depending on the performance requirements. The surface shape can be modified so that different bubble collapse geometries can be created.

The tip 150, including the hub 152 and the projection 154, may be transparent, in order to facilitate visualization by the operator through the material. The tip may be comprised of a polymeric material. As one example, the tip may be comprised of polycarbonate.

The projection 154 and the distal surface 160 may be asymmetrical about the longitudinal axis 118 of the shaft 110. This can allow a cutting or shaving action on one side of the instrument 100.

The projection 154 may be angled with respect to the longitudinal axis 118 of the shaft 110, i.e., not perpendicular to it. This can help facilitate insertion of the distal end 102 of the instrument 100 into the eye. That is, the operator can tilt the instrument 100 at a first angle to maneuver the projection 154 through the incision in the eye, and then tilt the instrument 100 at a second angle to maneuver the shaft 110 through the incision in the eye.

FIG. 6 shows the distal end of an ophthalmic instrument 200 in accordance with another embodiment of the disclosure. The ophthalmic instrument 200 may be the same as ophthalmic instrument 100 except that instead of the tip 150 the irrigation sleeve 220 incorporates a projection 254 with a distal surface 260. Thus, the projection 254 is part of the irrigation sleeve 220. The distal surface 260 functions similarly as the distal surface 160. In this illustrated example, the irrigation sleeve 220 has a center hole that provides an entranceway to the channel of the shaft 110 for aspiration. In this illustrated example, the optical fiber 140 is located inside of the shaft 110 and inside of the center hole of the irrigation sleeve 220. In an alternative example, the irrigation sleeve 220 again has a center hole that provides an entranceway to the channel of the shaft 110 for aspiration, but the optical fiber 140 is located outside of the shaft 110, and the optical fiber 140 is located either inside or outside of the center hole of the irrigation sleeve 220.

The irrigation sleeve 160, 260, including the projection 154, 254, may be transparent, in order to facilitate visualization by the operator through the material. The projection 154, 254 may be formed of the same material or a different material as the irrigation sleeve 160, 260, e.g., a polymeric material such as polycarbonate or an elastomeric material such as silicone rubber.

As with the projection 154, the projection 254 and the distal surface 260 may be asymmetrical about the longitudinal axis 118 of the shaft 110. This can allow a cutting or shaving action on one side of the instrument 100. Also, the projection 254 may be angled with respect to the longitudinal axis 118 of the shaft 110, i.e., not perpendicular to it, to facilitate insertion of the distal end of the instrument 200 into the eye, as described above.

In a method of performing an ophthalmic surgical procedure, the operator inserts a distal end of an ophthalmic instrument 100, 200 into the eye of a patient toward a treatment area. The operator positions the distal end of the ophthalmic instrument 100, 200 adjacent the treatment area such that a distal end of the optical fiber faces the treatment area and such that a distal surface 160, 260 of the projection 154, 254 faces the treatment area. The operator delivers laser energy through the optical fiber to the treatment area. The distal surface 160, 260 of the projection acts to inhibit bubbles formed during the procedure from moving distally away from the distal end of the ophthalmic instrument 100, 200.

As would be understood by persons of ordinary skill in the art, systems and methods as disclosed herein have advantages over prior systems and methods. For example, systems and methods as described herein may improve followability and laser action, improving the ease, time, efficiency, accuracy, outcome, and/or cost of the procedures.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. An ophthalmic instrument comprising:
   a shaft having a distal end adapted to be inserted into an eyeball of a patient toward a treatment area;
   an optical fiber for delivering laser energy to the treatment area, the optical fiber having a distal end adapted to be positioned facing the treatment area during use of the ophthalmic instrument; and
   a projection located at the distal end of the shaft, the projection having a distal surface in proximity to the distal end of the optical fiber, wherein:
      the distal surface is adapted to be positioned facing in a distal direction towards the treatment area during use of the ophthalmic instrument,
      the distal surface is concave, and the distal surface is configured to minimize repulsion during use of the ophthalmic instrument by changing bubble dynamics.

2. The ophthalmic instrument as recited in claim 1, wherein the shaft has an end face at its distal end, wherein a surface area of the distal surface of the projection is at least two times greater than a surface area of the end face of the shaft.

3. The ophthalmic instrument as recited in claim 2, wherein the surface area of the distal surface of the projection is at least eight times greater than the surface area of the end face of the shaft.

4. The ophthalmic instrument as recited in claim 1, wherein the distal surface of the projection has a length of 0.020 inches to 0.090 inches and a width of 0.020 inches to 0.060 inches.

5. The ophthalmic instrument as recited in claim 1, wherein the shaft is tubular, and wherein the shaft is adapted for aspiration from the treatment area.

6. The ophthalmic instrument as recited in claim 5, wherein the optical fiber is located inside of the shaft.

7. The ophthalmic instrument as recited in claim 5, wherein the optical fiber is located outside of the shaft.

8. The ophthalmic instrument as recited in claim 1, wherein the ophthalmic instrument comprises a tip positioned on the distal end of the shaft, and wherein the projection is part of the tip.

9. The ophthalmic instrument as recited in claim 8, wherein the tip is transparent.

10. The ophthalmic instrument as recited in claim 9, wherein the tip is comprised of a polymeric material.

11. The ophthalmic instrument as recited in claim 10, wherein the tip is comprised of polycarbonate.

12. The ophthalmic instrument as recited in claim 1, wherein the ophthalmic instrument comprises an irrigation sleeve.

13. The ophthalmic instrument as recited in claim 12, wherein the irrigation sleeve comprises a proximal hub adapted to be coupled to a housing of the ophthalmic instrument and a distal tube adapted to fit around the shaft.

14. The ophthalmic instrument as recited in claim 12, wherein the projection is part of the irrigation sleeve.

15. The ophthalmic instrument as recited in claim 14, wherein the irrigation sleeve is comprised of an elastomeric material.

16. The ophthalmic instrument as recited in claim 15, wherein the irrigation sleeve is comprised of silicone rubber.

17. The ophthalmic instrument as recited in claim 1, wherein the shaft has a longitudinal axis, and wherein the projection is asymmetrical about the longitudinal axis of the shaft.

18. The ophthalmic instrument as recited in claim 1, wherein the shaft has a longitudinal axis, and wherein the projection is angled with respect to the longitudinal axis of the shaft.

19. An ophthalmic instrument comprising:
a shaft having a distal end adapted to be inserted into an eye of a patient toward a treatment area;
an irrigation sleeve comprising a proximal hub adapted to be coupled to a housing of the ophthalmic instrument and a distal tube adapted to fit around the shaft;
an optical fiber for delivering laser energy to the treatment area, the optical fiber having a distal end adapted to be positioned facing the treatment area during use of the ophthalmic instrument; and
a projection located at the distal end of the shaft, the projection having a distal surface in proximity to the distal end of the optical fiber, the distal surface adapted to be positioned facing the treatment area during use of the ophthalmic instrument,
wherein the distal tube of the irrigation sleeve has a distal end, an end opening at its distal end adapted to fit around the distal end of the shaft, and at least one side opening at its distal end proximate to the end opening adapted for irrigation fluid to flow therethrough.

20. A method of performing an ophthalmic surgical procedure, the method comprising:
inserting a distal end of an ophthalmic instrument into an eye of a patient toward a treatment area, the ophthalmic instrument comprising a shaft, an optical fiber, and a projection;
positioning the distal end of the ophthalmic instrument adjacent the treatment area such that a distal end of the optical fiber faces the treatment area and such that a distal surface of the projection faces in a distal direction towards the treatment area, wherein the distal surface is concave; and
delivering laser energy through the optical fiber to the treatment area;
wherein the distal surface of the projection inhibits bubbles formed during the procedure from moving distally away from the distal end of the ophthalmic instrument.

* * * * *